United States Patent
Paek et al.

(10) Patent No.: US 7,300,802 B2
(45) Date of Patent: Nov. 27, 2007

(54) MEMBRANE STRIP BIOSENSOR SYSTEM FOR POINT-OF-CARE TESTING

(75) Inventors: Se Hwan Paek, Seoul (KR); Jung Hwan Cho, Incheon (KR); Ser Ka Kim, Seoul (KR)

(73) Assignee: Biodigit Laboratories Corp., Seoul 136-701 (KR)

( * ) Notice: Subject to any disclaimer, the term of this patent is extended or adjusted under 35 U.S.C. 154(b) by 431 days.

(21) Appl. No.: 10/827,884

(22) Filed: Apr. 20, 2004

(65) Prior Publication Data
US 2004/0214253 A1 Oct. 28, 2004

(30) Foreign Application Priority Data
Apr. 25, 2003 (KR) ...................... 10-2003-0026227

(51) Int. Cl.
*G01N 33/53* (2006.01)

(52) U.S. Cl. ...................... 436/514; 436/518; 436/169; 436/170; 436/810; 436/808; 436/823; 422/56; 422/58; 422/60; 422/82.02; 204/403.01; 204/403.03; 204/403.05

(58) Field of Classification Search ................ 436/518, 436/514, 169, 170, 808, 823; 422/56–60, 422/82.02; 204/403.01, 403.03, 403.06, 204/403.05
See application file for complete search history.

(56) References Cited

U.S. PATENT DOCUMENTS 5,264,180 A * 11/1993 Allen et al. .................... 422/56

(Continued)

OTHER PUBLICATIONS

Paek et al., "Performance Control Strategies of One-Step Immuno-Chromatographic Assay System For *Salmonella typhimurium*," Analytical Letters 32(2) 335-360 (1999).

(Continued)

Primary Examiner—Bao-Thuy L. Nguyen
(74) Attorney, Agent, or Firm—Heslin Rothenberg Farley & Mesiti P.C.; Kathy Smith Dias

(57) ABSTRACT

The present invention relates to a biosensor for point-of-care testing (POCT) whose detection sensitivity was remarkably improved by introducing to membrane strip chromatographic assay system a successive cross-flow procedure for immune reaction and enzymatic reaction. The present invention relates to a membrane strip biosensor system that comprises
(a) a membrane pad (10) for sample application,
(b) a membrane pad (20) for release of detection binding component, wherein the membrane pad (20) contains label-linked binding component for detection in a dry state,
(c) a signal generation membrane pad (30) with immobilized binding component for capture,
(d) a membrane pad (40) for absorption of vertical flow medium,
(e) a membrane pad (50) for the supply of substrate solution for enzyme,
(f) a membrane pad (60) for absorption of horizontal flow medium and
(g) substrate solution,
wherein the system has a cross-arrangement of two groups of the membrane pads,
(I) one group of vertically arranged pads, wherein the pad (10) is partially superimposed and fixed in length at the end of the pad (20), and the pad (20) and the pad (40) are partially superimposed and fixed in length at the both ends of the signal generating membrane pad (30), respectively; and
(II) the other group of horizontally arranged pads, wherein the pad (50) and pad (60) are, at the time of signal generation, partially superimposed and fixed at the both lateral sides of the signal generation membrane pad (30), respectively.

15 Claims, 12 Drawing Sheets

U.S. PATENT DOCUMENTS

| | | | | |
|---|---|---|---|---|
| 5,275,785 A | * | 1/1994 | May et al. | 422/56 |
| 5,648,274 A | * | 7/1997 | Chandler | 436/514 |
| 5,726,010 A | * | 3/1998 | Clark | 435/5 |
| 5,753,517 A | | 5/1998 | Brooks et al. | 436/514 |
| 5,837,546 A | * | 11/1998 | Allen et al. | 436/169 |
| 5,853,670 A | * | 12/1998 | Bunce | 422/100 |
| 5,997,817 A | * | 12/1999 | Crismore et al. | 204/403.1 |
| 6,087,184 A | * | 7/2000 | Magginetti et al. | 436/514 |
| 6,222,619 B1 | | 4/2001 | Herron et al. | 356/39 |
| 6,271,040 B1 | | 8/2001 | Buechler | 436/170 |
| 6,478,938 B1 | | 11/2002 | Paek et al. | 204/403 |

OTHER PUBLICATIONS

Watanabe et al., "Monoclonal-based enzyme-linked immunosorbent assay and immunochromatographic rapid assay for salinomycin," Analytica Chimica Acta 437 31-38 (2001).

Ono et al., "A highly sensitive quantitative immunochromatography assay for antigen-specific IgE," Journal of Immunological Methods, 272 211-218 (2003).

Sanchez et al., "P-phenol derivatives as enhancers of the chemiluminescent luminal-horseradish peroxidase-$H_2O_2$ reaction: substituent effects," Journal of Luminescence 65 33-39 (1995).

Wang et al., "Silver-Enhanced Colloidal Gold Electrochemical Stripping Detection of DNA Hybridization," Langmuir 17 5739-5741 (2001).

Liang et al., "Colorimetric detection of protein microarrays based on nanogold probe coupled with silver enhancement," Journal of Immunological Methods 285 157-163 (2004).

Laitinen et al., "Affinity immunosensor for milk progesterone: identification of critical parameters," Biosensors & Bioelectronics 11(12) 1207-1214 (1996).

Castillo-Ortega et al., "Conductometric uric acid and urea biosensor prepared from electroconductive polyaniline-poly(n-butyl methacrylate) composites," Sensors and Actuators B 85 19-25 (2002).

Janasek et al., "Chemiluminometric Flow Injection Analysis procedure for the enzymatic determination of L-alanine, α-ketoglutarate and L-glutamate," Biosensors and Bioelectronics 14 123-129 (1999).

Tanaka et al., "Relationship Between The Heme Active Site of Arthromyces Ramosus Peroxidase and Its Oxidation Activity For Luminol," Journal of Inorganic Biochemistry, p. 83.

Pizzariello et al., "Urea biosensor based on amperometric pH-sensing with hematein as a pH-sensitive redox mediator," Talanta 54 763-772 (2001).

* cited by examiner

MEMBRANE STRIP BIOSENSOR SYSTEM FOR POINT-OF-CARE TESTING

TECHNICAL FIELD

The present invention relates to a biosensor for point-of-care testing (POCT) whose analytical performances were remarkably improved by introducing, into membrane strip chromatographic assay system, a successive cross-flow procedure for immune reaction and other reactions for signal generation.

BACKGROUND ART

Measurement of disease marker substances (metabolites, proteins, cells etc.) present in low concentrations in a body fluid (blood, urine etc.) is generally carried out by employing biological reactions such as enzymatic reaction and antigen-antibody binding. Since enzyme and antibody exhibit very high reaction specificities of selectively recognizing their reaction partners and high reaction efficiencies, determination of analytes in a complex medium becomes possible. It is very important to seek development of diagnostic system based on such reaction characteristics so that early diagnosis of disease and adequate treatment of the disease in its early stage may be conducted. However, as most of the diagnostic systems require handling of reagents and devices, their use is limited to laboratories and further expert knowledge is necessary for conducting the testing.

Recently, as a category of immunoassay, the need of self-diagnosis at home as well as testing at the point of care such as doctor's office or emergency room for marker substances such as hormones, proteins and microorganisms that may indicate symptoms and progress of disease, is rapidly growing (Reference: C. P. Price et al., Principles and Practice of Immunoassay, 1997, page 579-603, Macmillan Reference Ltd., London). To this end, development of immunoassay system that does not require any expert knowledge and complex procedure, is simple to use, and provides quick response has been necessary. Such diagnostic performances could be achieved by an immuno-chromatography method that employs a microporous membrane for immobilizing a binding protein (e.g. antigen or antibody) (Reference: R. Chen et al., 1987, Clin. Chem. Vol. 33, Page 1521-1525; M. P. A. Laitinen, 1996, Biosens, Bioelectron., Vol. 11. 1207-1214: S. C. Lou et al., 1993, Clin. Chem., Vol. 39, 619-624; S. H. Paek et al., 1999, Anal. Lett., Vol. 32. 335-360). In this analytical format, when analyte-containing specimen is absorbed from the bottom end of the membrane strip, the analyte is transported to the layer of immobilized binding protein by the capillary action through membrane pores. A binding reaction between the antigen and antibody occurs on the surface of solids, and unbound molecules are subsequently separated by the medium flow. As the transfer of the reactant is accelerated by the lateral flow of medium, the membrane strip immuno-chromatography method based on the above principle provides a quick analysis of analyte and convenience of one-step detection where the analysis can be completed upon sample application alone.

The demand for such one-step diagnostic system has been well reflected in rapid growth of market of diagnostic kits for pregnancy and ovulation, and as establishment of internet-based telediagnosis and prescription system is soon expected, home monitoring system of diseases such as adult disease requiring periodical examination will be required as a key element of health care. However, current home-version diagnostic reagents are mostly at level of performing simple immuno-chromatographic assay and identifying the qualitative result of a color signal with naked eye, and thus unsuitable for analysis of indicator substances (protein marker etc.) requiring the determination of their concentrations. As conventional method that can be used for quantitative analysis, the color signal generated from gold colloids used as tracer can be converted to optical density using a conventional photometric transducing means (Reference: M. P. A. Laitinen, 1996, Biosens. Bioelectron., Vol. 11, 1207-1214), yet it has disadvantage, i.e. poor detection sensitivity in comparison to that of an enzyme-linked immunosorbent assay widely used in laboratories.

The disadvantage of low sensitivity from the point-of-care testing device can be overcome by using signal generator with high sensitivity such as fluorescent substance or radio-isotope. Actually, an immunoassay system was developed, where an immuno-chromatographic assay was performed using a detection antibody labeled with fluorescent substance and the assay result was measured with a fluorescence detector (Reference: U.S. Pat. No. 5,753,517). As this technique provided high sensitivity as well as no harmful effect, it has recently been applied to a point-of-care immunodiagnostic device that can be used in emergency room. (Reference: U.S. Pat. No. 6,271,040 B1). However, because fluorescence detectors are relatively too expensive and difficult to be reduced to a portable size, the system could be limitedly used in clinical laboratory of hospital or research laboratory, and thus when comparing with laboratory-version enzyme linked immunosorbent assay, there is no special advantage other than quick assay.

On the other hand, laboratory-version enzyme-linked immunosorbent assay essentially requires washing procedure for separating immune complexes from unreacted substance in the respective process of immunoassay, and further should carry out, separately, enzymatic reaction for signal generation. Consequently, such complex, multi-step procedure is clearly difficult to use for point-of-care testing.

The present invention makes it the object to provide a membrane strip biosensor technique which not only enables quick and simple assay required in point-of-care testing but also satisfies clinical needs for highly sensitive determination of analytes in specimen by applying to point-of-care testing the principle of laboratory-version enzyme-linked immunosorbent assay which provides advantage, being relatively cheap and high sensitivity.

DISCLOSURE OF THE INVENTION

The present invention relates to a membrane strip biosensor system that comprises (a) a membrane pad (10) for sample application, (b) a membrane pad (20) for release of detection binding component, wherein the membrane pad (20) contains label-linked binding component for detection in a dry state, (c) a signal generation membrane pad (30) with immobilized binding component for capture, (d) a membrane pad (40) for absorption of vertical flow medium, (e) a membrane pad (50) for the supply of substrate solution for enzyme, (f) a membrane pad (60) for absorption of horizontal flow medium and (g) substrate solution, wherein the system has a cross-arrangement of two groups of the membrane pads, (I) one group of vertically arranged pads, wherein the pad (10) is partially superimposed and fixed in length at the end of the pad (20), and the pad (20) and the pad (40) are partially superimposed and fixed in length at the both ends of the signal generating membrane pad (30), respectively; and (II) the other group of horizontally arranged pads, wherein the pad (50) and pad (60) are, at the time of signal generation, partially superimposed and fixed at the both lateral sides of the signal generation membrane pad (30), respectively.

The above membrane pads in the vertical arrangement are general ones used for the conventional immuno-chromatography method, and the additional membrane pads in the horizontal arrangement are only different. Such arranged membrane pads enable us to do a successive conduction of a reaction using the vertical flow, such as immune reaction, and the other reaction using the horizontal flow, such as enzymatic reaction, on the membrane strip biosensor system.

In the membrane strip biosensor system of the present invention, the horizontally arranged pads, (50) and (60) are either fixed from the first onto the signal generation membrane pad (30) combined with the vertically arranged pads or remained in a separated state at first and then fixed to the signal generation pad after the completion of the vertical flow reaction (e.g., immune reaction), which are utilized for performing the horizontal flow reaction (e.g., enzyme reaction).

In the above, in case the vertical arrangement pads are prepared separately from the horizontal arrangement pads, the connection of the two group pads can be carried out by fixing the vertical arrangement pads, (10), (20), (30) and (40), on a single plate and fixing the horizontal arrangement pads, (50) and (60) on the other plate, and then transferring any one plate over the other to be a cruciform.

Specifically, the membrane strip biosensor system according to the present invention can be prepared in such a form that the vertical arrangement pads, (10), (20), (30) and (40), are fixed inside the bottom part (72) of the holder (e.g., a plastic holder) of the system which has a signal detection window (78) and a substrate solution container-perforating needle (75), and the horizontal arrangement pads (50) and (60) are fixed on a horizontal arrangement pad-fixing frame (74) existing inside the top part (71) of the holder with a sample application hole, wherein the frame (74) is connected with a flow transfer button (73) present outside the top part (71), and a substrate solution container (76) containing the substrate solution that will be eventually added onto the substrate solution supplying membrane pad (50) (FIG. 7).

The operation principle of said membrane strip biosensor system is as follows:

When the horizontal arrangement pads are connected to the vertical arrangement pads in a cross-position via automatic or manual handling of the flow transfer button (73) after the completion of the vertical flow reaction, the substrate solution container (76) is broken by the substrate solution container-perforating needle (75) installed within the bottom part (72) of the holder, thereby the horizontal flow reaction is automatically conducted.

More specifically, the operation procedure of said membrane strip biosensor system is as follows:

First, when analyte-containing specimen is added through a sample application hole (77), immune reaction is conducted at the site with immobilized capture antibody by lateral flow through capillary pores of the vertical arrangement pads, and at this time the horizontal arrangement pads are maintained in a state without contact with the vertical arrangement pad by being fixed to the top part via the flow transfer button (73) (FIG. 7C). After the immune reaction, when the flow transfer button (73) is automatically or manually operated, the horizontal arrangement pad-fixing part (74) descends vertically, thereby the horizontal arrangement pads, (50) and (60), are respectively fixed at the left and right lateral side of the signal generation membrane pad (30) among the vertical arrangement pads, and at the same time, the substrate solution container-perforating needle (75) makes a hole on the bottom of the substrate solution container (76), automatically supplying an enzyme substrate to the pad (50) (FIG. 7D). The substrate then forms a horizontal flow and plays functions of washing unreacted components and enabling to generate a color signal from the enzyme included in the immune complexes formed with the capture antibody. The signal generated by the enzymatic reaction can be observed by the naked eyes through the signal detection window (78) and quantitatively determined using detection device based on colorimetry or other means for detection, such as luminometry and electrochemistry.

The membrane strip biosensor system in the present invention can be constructed in such mode that for electrochemical determination, additionally, an electrode can be either directly established on the signal generation membrane pad (30) or separately fabricated and combined with the pad at the time of signal detection.

In the membrane strip biosensor system, the substrate solution is prepared in a container fixed at a predetermined site on the top part of the holder of the system for facilitating its automatic supply of the substrate solution to the membrane pad (50) at the time of enzyme reaction. The substrate solution can also be prepared in a separate container from the analytical system for its manual supply.

As for material usable for said pads, anyone can be used, if suitable for the purpose of each pad. As a typical example, a glass fiber membrane can be used as the membrane pad (10) for sample application, the membrane pad (20) for conjugate release (The "conjugate" is used as the same meaning with the "labeled-binding component" in the present invention) and the membrane pad (50) for substrate solution supply; a nitrocellulose membrane can be used as the signal generation membrane pad (30); and a cellulose membrane can be used as the absorbent membrane pads, (40) and (60).

In the above, the membrane pad (20) for conjugate release comprises at least, a binding component for detection and a label (e.g., enzyme, fluorecein, radio isotope) for signal generation.

The label-linked binding component for detection, which is contained the membrane pad (20) in a dry state, comprises either i) the conjugate of a label with a binding component for detection, or ii) a binding component for detection and the conjugate of a label with a secondary binding component specific to the binding component for detection.

The binding component for detection is a substance, reacting specifically with an analyte, such as antibody, enzyme, receptor, DNA. In addition, the binding component for capture is a substance specifically reacting with an analyte, and antibody, enzyme, receptor or DNA etc. can be enumerated as the component. Therefore, the analytical principle of the present invention and the biosensor system based thereon can be utilized for the construction of immunosensor, enzyme sensor, and DNA sensor employing enzymatic signal generation.

As signal generator, enzymes such as horseradish peroxidase, alkaline phosphatase, β-galactosidase, arthromyces ramosus peroxidase, glucose oxidase, urease, penicillin oxidase, and cholesterol oxidase; gold colloid particles; and metal ions such as $Co^{2+}$, $Cu^{2+}$, $Mg^{2+}$ and $Fe^{2+}$ or their compounds can be listed. Said substrate solution comprises chromogenic component, light-generating component, electrochemical signal-generating component, or silver compound; and conducts an action of the generation of color, color change, light emission, conductivity change, current change, or voltage change as signal.

Application of the membrane strip biosensor system of the present invention according to selection of a signal generator and substrate solution can be explained as follows.

In case of color detection-type photometric biosensor, as the signal generator, horseradish peroxidase, alkaline phosphatase, β-galactosidase, or arthromyces ramosus peroxidase can be used, and the substrate solution comprises a chromogenic substrate component specific to the respective enzyme, and the enzyme-substrate reaction generates a signal detectable by naked eyes, i.e., color or color change. Further, as an alternative to the enzyme-substrate reaction, a chemical reaction can be employed and as a typical example, a signal as mentioned above can be generated by catalytic reaction between gold and silver by using gold colloid as tracer and silver compound such as silver acetate as the substrate solution.

In case of light detection-type photometric biosensor, as tracer, horseradish peroxidase or arthromyces ramosus peroxidase can be used, and the substrate solution comprises a light-generating substrate component specific to the respective enzyme, e.g., luminol, and at the time of signal generation, a light signal detectable with naked eyes is generated by the enzyme-substrate reaction. In addition, as an alternative tracer to the enzyme that is indicated above, metal ions, i.e. $Co^{2+}$, $Cu^{2+}$, $Mg^{2+}$, $Fe^{2+}$, or their compounds can be used.

In case of electrochemical biosensor, glucose oxidase, urease, penicillin oxidase, or cholesterol oxidase can be used as the signal generator, and the substrate solution comprises an electrochemical signal-generating substrate component specific to the enzyme, and the enzyme-substrate reaction generates conductivity change, current change, or voltage change as signal.

The membrane strip biosensor system of the present invention can be explained in more detail regarding immunoassay as follows. Considering an example shown in FIG. 1, the membrane strip biosensor system based on the successive cross-flow of medium is composed of functional membrane pads which are respectively arranged in horizontal direction on the left and four different membrane strips which are connected in vertical direction with one another on the right. In the vertical arrangement, at the bottom, a glass fiber membrane pad (10) for sample application is positioned and, at the upper location, a glass fiber membrane pad (20) containing detection antibody (22)-enzyme (21) conjugate in a dry state is arranged. The conjugate exhibits immobility while existing in a dry state, yet upon contact with an aqueous medium, it is instantly dissolved and participates in antigen-antibody reaction in the liquid phase. At the upper position, a nitrocellulose membrane pad (30), where the capture antibody (31) and a secondary antibody (32) specific to the detection antibody are respectively immobilized on predetermined sites, is located and here, eventually a signal in proportion to the concentration of an analyte and a constant signal as control irrelevant to the analyte concentration are independently generated at the respective site. At the top location, a cellulose membrane pad (40) as absorbent is positioned to maintain the lateral flow by the capillary action through micropores in the membrane pads listed above. Each membrane pad are partially superimposed each other, arranged on a plastic film, and fixed by a double-sided tape to prepare a functional immuno-strip. In addition, separately from the immuno-strip, a glass fiber membrane pad (50) for supplying substrate for enzyme as tracer or an aqueous medium for signal amplification that will be eventually located at the left side of the nitrocellulose membrane pad (30) and a cellulose membrane pad (60) for absorption of substrate solution that will be located at the right side thereof in order to maintain the flow of substrate solution by the capillary action are prepared. Such horizontal arrangement pads, initially, are not in contact with the immuno-strip main body thereby immune reaction is first performed in the vertical direction alone through the immuno-strip, and the subsequent connection of the left and right pads allows the enzymatic reaction to be conducted in horizontal direction alone.

Analytical Concept of the Membrane Strip Biosensor System

Analytical procedure that consists of four steps using the membrane strip biosensor system constructed as described above is shown in FIG. 2. First, when the bottom end of the immuno-strip is immersed in an analyte-containing specimen (e.g., serum, plasma, whole blood), the specimen is absorbed inside the system through the sample application pad and the medium is transferred along the strip by the capillary action in the vertical direction (FIG. 2A). When the medium reaches the glass membrane pad with the accumulated antibody conjugate in a dry state, the conjugate is instantly dissolved and a primary immune complex is formed by the antigen (i.e., analyte)-antibody reaction in the liquid state. When this immune complex is transferred to the signal generation pad in the upper position, by the reaction with the immobilized capture antibody, it is captured on the solid surface to form a sandwich type immune complex, and unbound substances are separated by the medium flow. Second, the immuno-strip is connected with the horizontal arrangement pads (FIG. 2, B). This can be performed by transferring the vertical arrangement pads or the horizontal arrangement pads using a pad-fixing frame. Third, an enzyme substrate solution is added automatically or manually to the substrate solution supply pad, and the horizontal flow is initiated, which allows the solution to be absorbed into the substrate solution absorption pad through the signal generation pad (FIG. 2, C). Fourth, the substrate is supplied to the enzyme, tracer, included in the sandwich immune complex formed with the capture antibody immobilized on the nitrocellulose membrane, thus a signal in proportion to the analyte concentration and the control signal are independently generated by the catalytic reaction (FIG. 2, D). The signal is quantified using an adequate detector (e.g., color detector, light detector, or electrochemical detector) according to the type of the signal generator selected to determine the analyte concentration.

The main objective of 'the membrane strip biosensor system based on a vertical-horizontal cross-flow' devised in the present invention is to combine the signal generation technology using catalyst such as enzyme as tracer with the immuno-chromatographic analytical method such that point-of-care testing with a high sensitivity can be carried out. In an ordinary enzyme-linked immunosorbent assay using microwells as a solid matrix, unreacted components are separated from immune complex after antigen-antibody reactions and the substrate for an enzyme label included in the complex is then added to perform the catalytic reaction to generate a signal. However, such separation of the immune complex and signal generation from the enzyme is difficult to achieve in case of the conventional immuno-chromatographic assay system, which is dependent only on the vertical flow. If the enzyme substrate exists in advance or is added before the complete separation of the immune complex, a nonspecific signal is generated regardless of the analyte concentration. Therefore, the two procedures, the separation of immune complex and the signal generation, should be entirely successively carried out, step by step. Such requirement is satisfied by introducing the cross-flow concept developed in the present invention, and this is inventive in that it enables the subsequent supply of the substrate which was impossible to achieve by the vertical flow alone in an immuno-strip. In this new format of assay, automation of the assay procedure is possible so that a separate washing process or handling of reagent may be eliminated and analysis can be completed in a short period of time (e.g., 15 min) after sample application, and further accurate assay results can be obtained owing to the use of enzyme as a sensitive signal generator.

Various flow paths for supplying the enzyme substrate solution are shown in FIG. 3. Besides the horizontal flow (FIG. 3, A) through the signal generation pad on the immuno-strip, a horizontal, diagonal flow (FIG. 3, B) by adequate arrangements of the substrate solution supply pad and absorbent pad can also be induced. In addition, after conducting the immune reaction and then removing the components of immuno-strip except the signal generation pad, the substrate solution supplying pad and adsorption pad are arranged in length, thereby the substrate solution can be supplied in various vertical flow (FIGS. 3, C, D and E). Among such different flow paths, considering simultaneous multiple signal generation and effectiveness in designing the novel analytical system, the supply of the enzyme substrate solution through horizontal flow is preferred.

Advantages of the membrane strip biosensor system for point-of-care testing developed in the present invention in comparison to other conventional systems, are as follows. First, when comparing the enzyme tracer with other calorimetric signal generator such as gold colloid and latex particles, the enzyme generates a signal by the catalytic reaction, and thus provides an amplification effect. Therefore, the detection of analyte employing the novel biosensor is highly sensitive as in case of biosensor using fluorescent substance as signal generator. Second, if a suitable enzyme-substrate reaction is employed, the detector for measuring the signal generated by the reaction relatively cheap in comparison to a fluorescence detector and can be reduced to a portable size. Third, various enzymes can be used as tracer in the analysis and thus, as explained above, different signals such as change in color, light, current, voltage, and conductivity can be generated. This provides the flexibility that an enzyme can be selected as tracer in accordance with available signal detecting device and technology.

Color Detection-type Photometric Biosensor

The membrane strip biosensor system as explained above can be employed for the construction of a color signal detection-type photometric biosensor as an application of the same analytical concept. Such biosensor independently achieves the enzymatic reaction for signal generation on the membrane strip as in the conventional enzyme-linked immunosorbent assay (ELISA) using microwells as solid matrix for protein immobilization, thereby providing advantages that can be achieved from the both assay systems, i.e., high sensitivity as in ELISA and quick response as in ordinary immuno-chromatographic assay. In the color detection-type sensor, the intensity of color signal sensitively generated on the membrane in proportion to the analyte concentration within sample can be determined based on reflectance photometry. Therefore, when comparing with a fluorescence detection-type system used conventionally for quantitation, the color detection-type sensor maintaining comparable analytical performances is relatively cheap and uses small-sized signal detector, thus can be applied to point-of-care testing.

The analytical principle of the color detection-type biosensor is described in detail in FIG. 4. When analyte-containing sample (e.g., blood) is absorbed from the bottom end of the immuno-strip via the vertical flow as explained above, the analyte reacts with the detection antibody-enzyme conjugate, the primary immune complex formed is captured by the capture antibody immobilized on the signal pad, and the unreacted components are then separated by the medium flow (FIG. 4, A). Amount of the captured detection antibody-enzyme conjugate is proportional to the analyte concentration, and thus, eventually a signal proportional to it is generated. Excess conjugate separated by the vertical flow is captured by the secondary antibody immobilized in the upper region of the same strip. The signal at this site can be kept constant regardless of the analyte concentration, and it can be utilized as the control signal. For signal generation from the enzyme conjugate, the enzyme substrate is supplied through the horizontal flow as described above, and then all other components except the immune complexes captured by the immobilized antibodies are eliminated and, at the same time, signals are generated by the enzyme included within the captured immune complexes (FIG. 4, B). The intensity of color signal generated on the membrane strip is determined by applying a light with a constant wavelength and measuring the reflected light which deceases in proportion to the color intensity, using a photometric detector (e.g., photodiode, charge-coupled device etc.) (FIG. 4, C).

As enzymes usable for the generation of the color signal, horseradish peroxidase (HRP), alkaline phosphatase, β-galactosidase, and arthromyces ramosus peroxidase (ARP), widely used in ELISA, can be listed. These enzymes generate color signals as results of catalytic reactions, and the substrates that can be used for such purpose are various for each enzyme. For example, in case of using HRP, tetramethylbenzidene (TMB), diaminobenzidene (DAB), and 4-chloro-1-naphthol (4C1N) can be used as insoluble chromogenic substrates in the presence of hydrogen peroxide. Respective substrate require different optimal reaction conditions, thus an adequate substrate can be selected by considering its analytical characteristics and the requirements of the biosensor.

As labeling methods of enzyme, besides the method of directly conjugating an enzyme with the detection antibody as mentioned above, an indirect method of using a secondary antibody specific to the detection antibody could be enumerated. In this case, the detection antibody and a secondary antibody-enzyme conjugate are accumulated respectively, in a spatial separation, on the conjugate pad of immuno-strip to construct an assay system. At the time of assay, the enzyme conjugate specifically reacts with the primary immune complex between the detection antibody and analyte that was then captured by the capture antibody immobilized on a definite site of the signal generation pad. This method can resolve inconvenience that conjugation between the detection antibody and an enzyme should be conducted every time for different analytes. In addition, the detection antibody can also be used via conjugation with gold colloid, and thus the detection antibody-gold conjugate and the secondary antibody-enzyme conjugate can be accumulated in separate locations on the conjugate pad of the immuno-strip. In case of applying this method to the membrane strip biosensor system, a red color signal is generated, after assay, from gold colloids in proportion to the concentration of the primary immune complex between analyte and the gold conjugate which is subsequently captured by binding to the immobilized antibody during the vertical flow, thus assay progress can be followed by naked eyes. Further, in case one or more detection antibody molecules are being bound on the gold colloid surface, the secondary antibody-enzyme conjugate can be bound in proportion to the number of the detection antibody molecules, thus providing signal amplification effect.

As another method for signal generation, the binding reaction between streptavidin and biotin can be employed and, typically, streptavidin is conjugated with the detection antibody and biotin is coupled to enzyme. Because the reaction between streptavidin and biotin exhibits the highest affinity among known biological reactions so far, it provides an advantage, i.e., signal amplification effect, comparing to the method of using the secondary antibody. When constructing an assay system, a signal generation method mentioned above can be selected depending on the requirements for the assay system such as the lower detection limit of analyte, dynamic range, analysis time and, expense.

In another format of color signal detection-type biosensor, for signal generation, a chemical reaction such as catalytic reaction between gold and silver can be employed as an alternative to the enzymatic reaction, and as typical reactants, gold colloid and silver acetate can be listed (Reference: Patel N et al., 1992, Ann. Clin. Biochem. Vol. 29, Page 282-286, Rocks. BF et al., 1991, Ann. Clin. Biochem. Vol. 28, Page 155-159). As in the conventional immuno-chromatographic method, an immuno-strip is prepared by using the detection antibody-gold colloid conjugate as signal generator and a color signal is generated from the gold in proportion to the analyte concentration through the primary vertical flow. When a silver acetate solution is supplied through the secondary horizontal flow based on the cross-flow concept, silver is accumulated, via catalytic reaction, onto the surface of gold colloid bound on the site of the capture antibody and thus noticeably amplifies the color signal. Such an effect is identical to that of the assay system using an enzyme as signal generator, and an assay system with high sensitivity can be readily constructed by subsequently supplying a chemical substance such as silver acetate that can amplify the gold color signal simply based on the cross-flow method without using enzyme, biological material. Introduction of such a method provides a significant advantage that the determination of analyte in a trace concentration becomes possible, which could not be achieved by means of a naked eye-identification of the gold color. The amplified color signal can be measured by a reflectance photometry as in the case of using enzyme.

Light Detection-type Photometric Biosensor

As another format of the membrane strip biosensor system developed in the present invention, it can be used for the construction of light detection-type photometric biosensor. When compared with the color detection-type biosensor mentioned above, such a biosensor employs tracer which itself generates a light signal. Thus this format of biosensor does not require a light source, which makes detector simpler and cheaper. The detection principle and variability of the assay system are identical to those of the color detection-type biosensor explained above, yet selection of suitable signal generators are necessary so that light signals in proportion to the analyte concentration may be generated. As specifically shown in FIG. 5, arthromyces ramosus peroxidase (ARP), an enzyme, can be used as signal generator, and this enzyme generates by reaction with luminol a light signal that can be measured at the maximum absorbance of 427 nm (Reference: Kim, Pisarev, and Egorov, 1991, Anal. Biochem. Vol. 199, Page 1-6). The intensity of the light signal is about 500-fold in the sensitivity compared to that from HRP which is ordinarily used for color generation. As alternative to enzyme, metal ions ($Co^{2+}$, $Cu^{2+}$, $Mg^{2+}$, $Fe^{2+}$, etc.) can be used, and these are cheap and further generate more sensitive light signal than does enzyme (Reference: D. Junsaek, U. Spohn, 1999, Biosensors & Bioelectronics, Vol. 14, Page 123-129).

The light signal generation method using enzyme or metal ion as tracer can be applied to the cross-flow system of the present invention. After the vertical flow is progressed for antigen-antibody reactions, the horizontal flow is sequentially progressed for supplying the substrate solution (FIG. 5, A). At this time, the unbound components except the immune complexes bound to the antibody immobilized on the membrane is washed and, at the same time, a light signal is generated from the tracer included in the captured immune complexes. In the case of ARP used as tracer, a substrate solution, containing luminol and hydrogen peroxide, adjusted to an optimal acidity is employed. A detection means such as photodiode is carried near the signal generation pad to measure the generated signal (FIG. 5, B) under the dark condition for minimization of noise. After detection of the signal by a photometric detector and conversion to an electric signal, the analyte concentration in a specimen is determined based on the standard curve showing the signal change against the analyte concentration.

In the case of constructing the light detection-type biosensor, labeling methods of tracer on the antibody molecule and arrangement of the analytical components are identical to those explained above in detail for the construction of the color detection-type biosensor.

Electrochemical Biosensor

The concept of the membrane strip biosensor system developed in the present invention can also be used for the fabrication of electrochemical biosensors as another application. Such biosensor uses as signal generator an enzyme, which induces a change of ionic concentration, charge density, or electrochemical potential via enzymatic conversion of substrate, and produces an electrochemical change as signal (Reference: M. M Castillo-Ortega et al., 2002, Sensors and Actuators B. Vol 85, page 19-25; Andrea Pizzariello et al., 2001, Talanta, Vol 54, Page 763-772). Electrochemical detector for such signal is relatively simple to use, cheap, and small-sized, yet as extra requirement, an electrode for electrochemical measurement should be directly installed on the immuno-strip or separately prepared to combine with the immuno-strip at the time of signal detection (Reference: J. H. Kim, S. H. Paek, 2000, Biosensors & Bioelectronics, Vol. 14, Page 907-915). The analytical principle of the assay system is identical to that of the photometric biosensors explained above and yet selection of a suitable signal generator is needed for the generation of an electrochemical signal in proportion to the analyte concentration.

Enzymes usable as tracer can be varied according to the method of electrochemical detection. For example, to induce a conductivity change as the signal, urease can be used. This enzyme increases ionic concentration by decomposing urea as the substrate into ammonium ion and carbonium ion, thereby a conductivity change in proportion to the analyte concentration is produced as the signal (FIG. 6). As another example, to generate an electric current change as the signal, an enzyme that oxidizes or reduces its substrate, i.e., glucose oxidase and cholesterol oxidase, can be used as tracer and a change of electron density via the enzymatic reaction is measured as a current change using an electrode. As another example, a change of electrochemical potential can be generated as the signal and a typical application thereof is to use as tracer enzymes modulating the hydrogen ion concentration, i.e., acidity, (glucose oxidase, urease, penicillin oxidase) and to measure the results of the enzymatic reaction using a pH electrode (Reference: Andrea Pizzariello et al., 2001, Talanta, Vol. 54, page 763-772). On the other hand, in the case of using urease as tracer, a selective membrane for the ammonium ion or carbonium ion produced by the decomposition of urea in this enzymatic reaction is installed on an electrode surface, thereby the change of chemical potential can be detected as the electric signal.

The analytical principle of the electrochemical biosensor is identical to that of the photometric biosensors as explained above, and as depicted in FIG. 6. When analyte-containing specimen is applied to the bottom end of the immuno-strip, the analyte forms the primary immune complex with the antibody-enzyme conjugate released from the conjugate pad and this, then forms the sandwich-type immune complex with the capture antibody immobilized on the signal generation pad. When the vertical flow for antigen-antibody reaction is stopped and switched to the horizontal flow, other components except the captured immune complex are removed, and at the same time, an electrochemical signal is generated by the reaction between the enzyme present in the captured immune complex and its substrate (FIG. 6, A). To detect such electrochemical signal, a suitable electrode that was already placed on the membrane or separately prepared is employed (FIG. 6, B) such that the signal-to-noise is maximized (FIG. 6, C). In addition, in the case of electrochemical analysis, since analytical conditions regarding electrode, such as material, shape, and size affect detection performances of the biosensor, physicochemical factors of the sensor should be optimized against the signal-to-noise ratio.

The membrane strip biosensor system based on the cross-flow which was conceived in the present invention as described above leads to the construction of various biosensors according to the suitable selection of enzyme as tracer. In the past, assay systems using membrane strip offered no way to provide the components necessary for an enzymatic reaction to generate a signal from enzyme as tracer and, thus construction of an efficient biosensor was difficult. This problem can be resolved by using the cross-flow concept developed in the present invention. That is, the cross-flow method enables the construction of various biosensors according to the enzyme tracer as well as a convenient, automatic supply of the enzyme substrate solution. Therefore, the enzyme-linked immunosorbent assay (ELISA), which could not be conventionally handled by ordinary persons due to a complex assay procedure and long assay time despite of its high sensitivity, can be conveniently performed on membrane strip. Additionally, it becomes possible according to the present invention to use various enzymes as signal generator, as an alternative to the previous fluorescence tracer requiring an expensive detector, thereby a cheap and small-sized detector can be employed.

Figure 1:
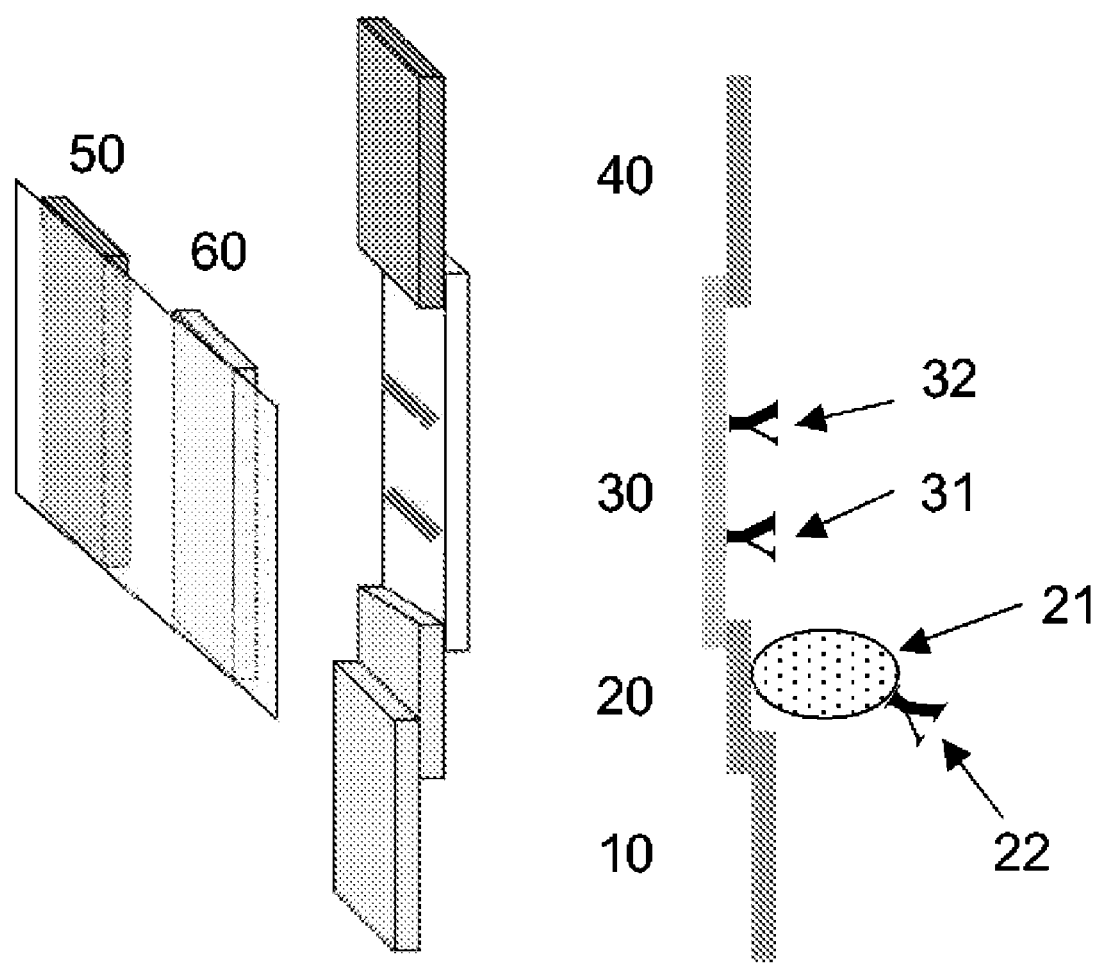
FIG. 1 shows components and arrangement of the membrane strip biosensor system conceived in the present invention.

1: analyte
10: membrane pad for sample application
20: membrane pad for release of label-linked detection binding component
21: signal generator (or tracer)
22: detection antibody
30: membrane pad for signal generation
31: capture antibody
32: secondary antibody specific to the detection antibody
33: light source
34: photometric detector
35: electrode for electrochemical signal detection
40: membrane pad for absorption of vertical flow medium
50: membrane pad for the supply of substrate solution
60: membrane pad for absorption of horizontal flow medium
71: top part of the holder
72: bottom part of the holder
73: flow transfer button
74: horizontal arrangement pad-fixing plate
75: substrate solution container-perforating needle
76: substrate solution container
77: sample application hole
78: signal detection window

BEST MODE FOR CARRYING OUT THE INVENTION

The following Examples support more specifically the content of the present invention and presents its usefulness through demonstration specific applications, yet never limits the scope of the present invention.

MATERIALS USED IN EXAMPLE

Materials used in Examples and their sources are as follows. Hepatitis B surface antigen (HBsAg), polyclonal antibody (produced from rabbit) and monoclonal antibody (produced from mouse) against HBsAg, and polyclonal antibody (produced from goat) to human serum albumin were purchased from Enzyme International (USA). Cardiac troponin I (cTn I) and antibodies specific to it, i.e., polyclonal antibody (produced from goat) and monoclonal antibody (produced from mouse) were purchased from Spectral (USA). Gold colloid (diameter 40 nm, 0.01%), sephadex gels, casein (sodium salt type, extracted from milk), bovine serum albumin (BSA, purification by heat shock process, fraction V), Tween 20, Triton X-100, human serum albumin (HSA) were supplied by Sigma (USA). Nitrocellulose membrane (pore size 12 µm) and glass fiber membrane, and cellulose membrane (3 MM chromatography grade) were purchased from Millipore (USA) and Whatman (USA), respectively. Streptavidin (SA), N-succinimidyl-3-[2-pyridyldithio]propionate (SPDP), succinimidyl 4-[N-maleimidomethyl]cyclohexane-1-carboxylate (SMCC), dithiotheritol (DTT), and N-hydroxysuccinimidyl (NHS)-LC-LC-biotin were obtained from Pierce (USA). Enzymes, i.e., horseradish peroxidase (HRP), arthromyces ramosus peroxidase (ARP) and urease were purchased from Calbiochem (USA). Substrates for each enzyme, i.e., tetramethylbenzidene (TMB) and luminol, urea were purchased from Moss (USA) and Sigma (USA), respectively. Other reagents used were of analytical grade.

Example 1

Synthesis of Antibody-colloidal Gold Conjugate

Acidity and antibody concentration of various reaction solutions were tested according to the standard protocol, and under optimal condition thus found, conjugate was synthesized (Reference: S. H. Paek et al., 1999, Anal. Lett., Vol. 32, 335-360).

Briefly, dialyzed solution of antibody (100 µg/ml, 0.8 ml) specific to HBsAg in a neutral pH buffer was added to gold solution (8 ml) adjusted to pH 9.0, and reacted for 30 min. Then, to this solution, 1 ml of 5% casein solution (casein-PB) prepared by dissolving it in 10 mM phosphate buffer (pH 7.4, PB) was added and reacted for 30 min. After the reaction solution was centrifuged at 15,000 rpm for 45 min, the supernatant was removed. To the remaining gold precipitates, casein-PB was added to adjust the final volume of the conjugate to 0.2 ml and stored at 4° C. until used.

Example 2

Synthesis of Antibody-enzyme Conjugate

Conjugation between an antibody specific to analyte and enzyme was performed by a chemical reaction using a cross-linker. After the antibody was reacted with SMCC in a 20-fold excess mole concentration for 4 h at 4° C., the excess SMCC was removed by Sephadex G-15 gel chromatography and the antibody was then directly conjugated with an enzyme activated as described below. For the activation of enzyme, the protein was dissolved in 5 mM EDTA-containing PB and reacted with SPDP in a 20-fold excess mole concentration for 1 h at room temperature. To introduce sulfhydryl group on the molecule, DTT (final 10 mM) was added to the reaction mixture and again reacted for 2 h at 37° C. Excess reagents were removed on Sephadex G-15 gel column. The two activated reactants, i.e., the antibody and the enzyme, were mixed to a mole ratio of 1:10 and reacted at 4° C. overnight. Purification of such synthesized antibody-enzyme conjugates was conducted using a column (1×20 cm) filled with Sephadex G-100 gel. The reaction mixture (1 ml) was injected into the column and eluted with PBS. Protein within each elution fraction was monitored by Bradford assay, and the synthesis and purification of the conjugate were finally confirmed by SDS-PAGE (7% gel) assay under non-reducing conditions.

Example 3

Signal Generation Pad with Immobilized Antibody

As signal generation pad, an optimal product of a nitrocellulose (NC) membrane toward immobilization efficiency and pore size was used. the NC membrane (pore size: 12 µm, Millipore) was used for the immobilization of antibody. As immobilization method, physical adsorption and chemical method can be used and an adequate method was eventually selected based on the results of experiments by considering convenience of the method and reproducibility. Antibody was immobilized on a predetermined site of NC membrane strip (7×25 mm) by physical adsorption. To a site (10 mm from the bottom) on the membrane, 1 mg/ml antibody (1.5 µL) diluted with PB containing 140 mM NaCl (PBS) was spotted by using micro-dispenser and then reacted for 1 h at room temperature. The strip with immobilized antibody was immersed in 0.5% casein dissolved in 100 mM Tris buffer (pH 7.6; Casein-Tris) for 1 h to block the residual surfaces, followed by washing three times with the tris buffer containing 0.1% triton X-100, and dried in the ambient air.

Example 4

Signal Generation Pad (with Immobilized Streptavidin)

As signal generation pad, the same NC membrane was used as explained in Example 3 for the immobilization of streptavidin (SA) in place of antibody. As immobilization method, since physical adsorption of SA showed a low yield of immobilization in preliminary experiments, a chemical method was employed. The NC membrane (7×25 mm) was immersed in 0.5% glutaraldehyde solution and reacted for 1 h and then washed three times with PBS. 10 mg/ml of SA (1 µL) was applied at a site of 1 cm from the bottom end by use of micro-dispenser, incubated in a box maintaining 100% humidity and reacted for 1 h at room temperature. The remaining steps were identical to those for the immobilization of antibody show in Example 3.

Example 5

Construction of Color Detection-type Analytical System 5-1. Construction of Immuno-strip An immuno-chromatographic assay system, where a signal depending on the concentration of analyte (HBsAg) is determined by naked eye identification or optical density measurement, was constructed using detection antibody-gold colloid conjugate used in Example 6-1 or the gold conjugate in the combination with secondary antibody-HRP conjugate (used in Example 6-2) as signal generator. The immuno-strip (FIG. 1) includes, from the bottom, a glass fiber membrane (7×20 mm) treated with 0.1% (v/v) Triton X-100, a glass fiber membrane (7×5 mm) with the labeled conjugate(s), a NC membrane (7×25 mm) with immobilized antibody, and a cellulose membrane (7×15 mm) as absorbent pad. Each contiguous membrane strip were partially superimposed and fixed on a plastic film by a double-sided tape.

5-2. Construction of Horizontal Arrangement Pad

Figure 2:
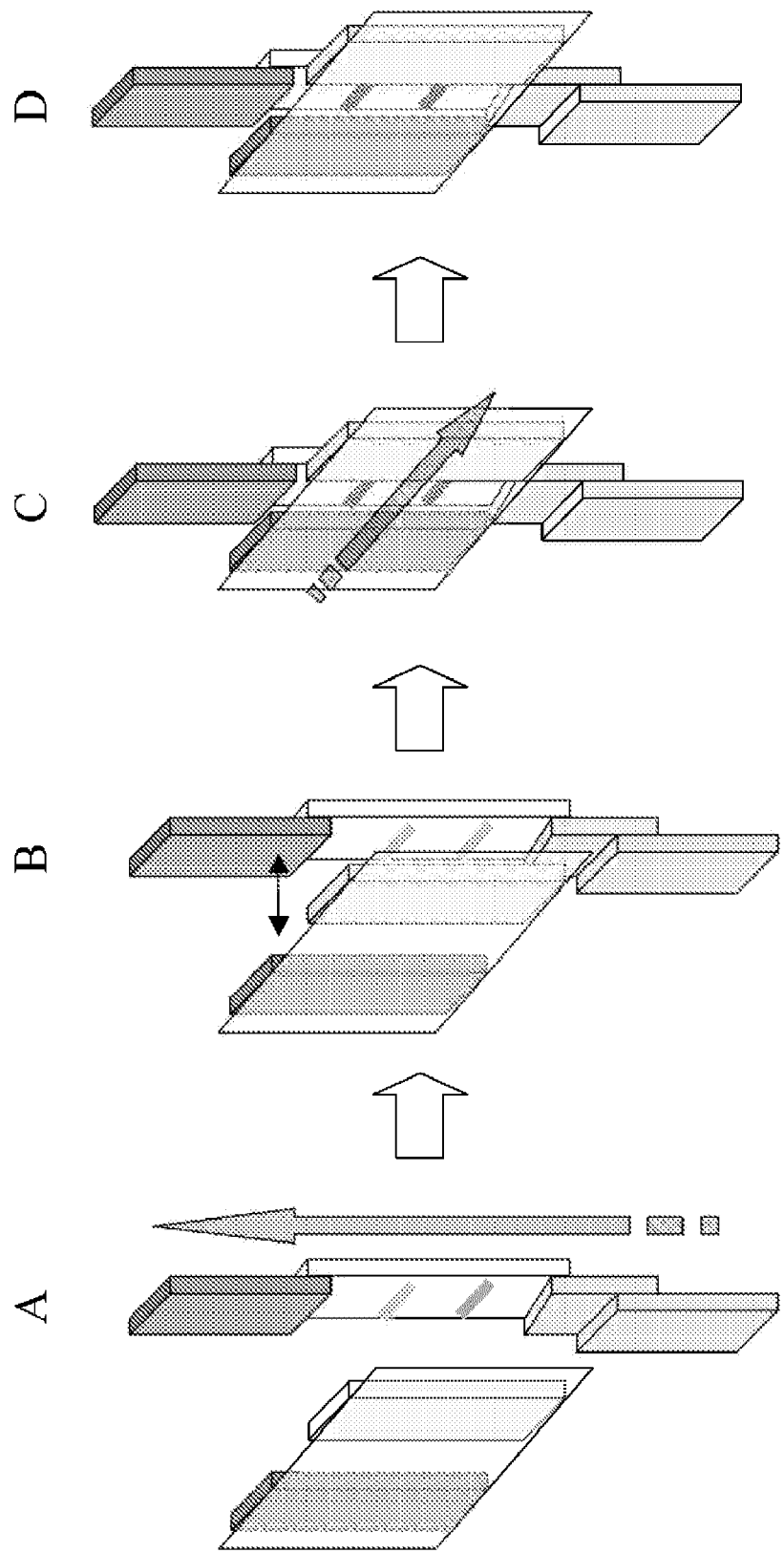
FIG. 2 shows a cross-flow chromatographic assay procedure of the membrane strip biosensor system, key points of the present invention, and its analytical principle based thereon. In this Figure, A depicts the absorption of sample and antigen-antibody reactions induced by the vertical flow of medium; B depicts the connection of the immuno strip with the horizontal arrangement pad; C depicts the supply of substrate solution for an enzyme used as label in the immunoassay; and D depicts the signal generated from the enzyme.
Figure 3:
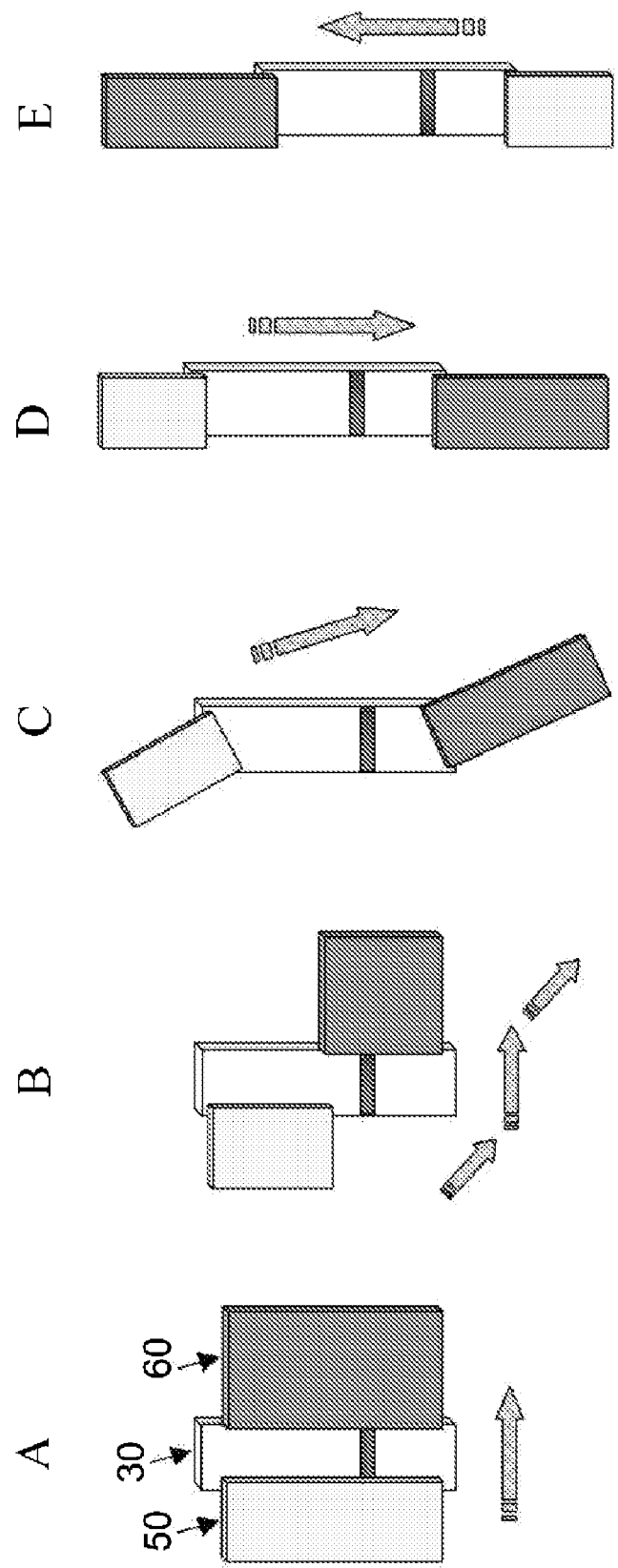
FIG. 3 shows various flow paths for supplying enzyme substrate solution, which are available in the analysis based on a dual-flow chromatographic method.
Figure 4:
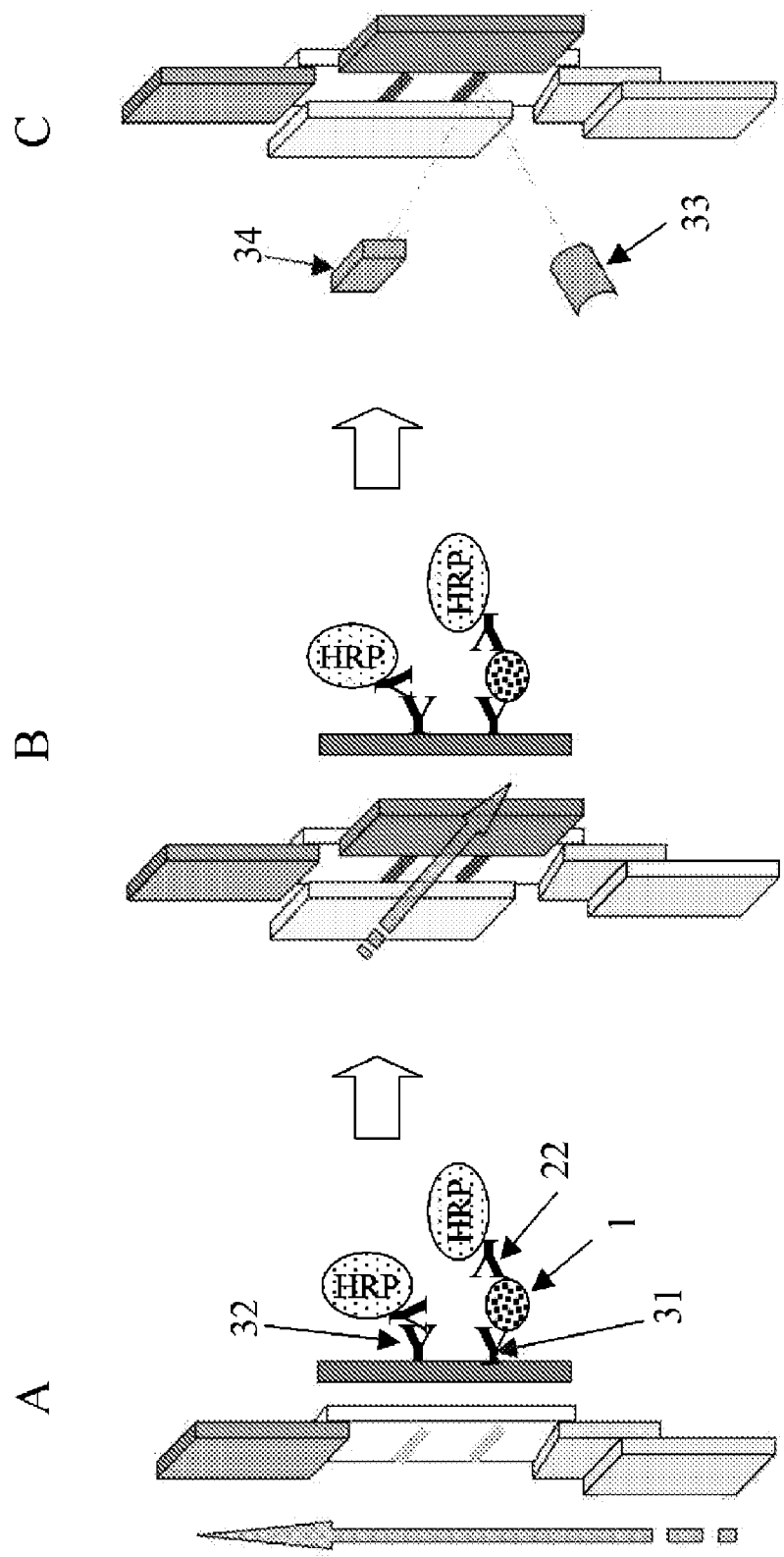
FIG. 4 shows the analytical principle of a color detection-type photometric biosensor according to the present invention that is based on the enzyme-linked immunosorbent assay method combined with the cross-flow chromatography. Herein, A describes the sample application and immune complexes formation by the vertical flow of medium, B enzymatic reaction for signal generation by the horizontal flow of the substrate solution, and C a color signal detection based on reflectance photometry.
Figure 5:
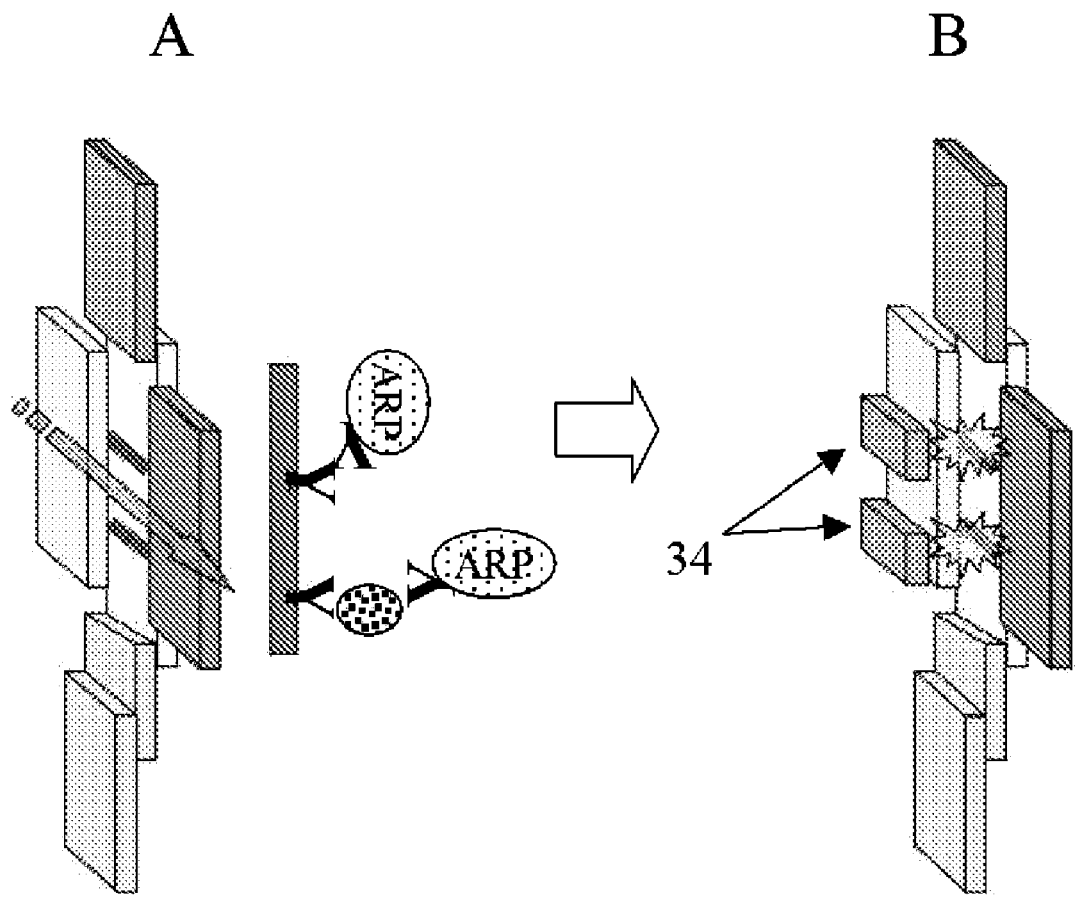
FIG. 5 shows the analytical principle of a light detection-type photometric biosensor in the present invention, which is based on the identical concept described in FIG. 4 except signal generation. Herein, A describes enzymatic reaction for signal generation by the horizontal flow and B a luminometric signal detection.

For the generation of color signal from HRP in case of use of the antibody-HRP conjugate, the horizontal arrangement pad were constructed using a glass fiber membrane (10×20 mm) for supplying the enzyme substrate containing hydrogen peroxide and TMB, and a cellulose membrane (15×20 mm) as absorption pad for inducing the cross-flow. The pads were spatially seperated from the immuno-strip explained above and the analytical system was designed in such a way that the horizontal pads, thereafter, were allowed to be in contact with the both lateral sides of the NC membrane, respectively, to induce the enzyme reaction (FIG. 2).

Example 6

Figure 8:
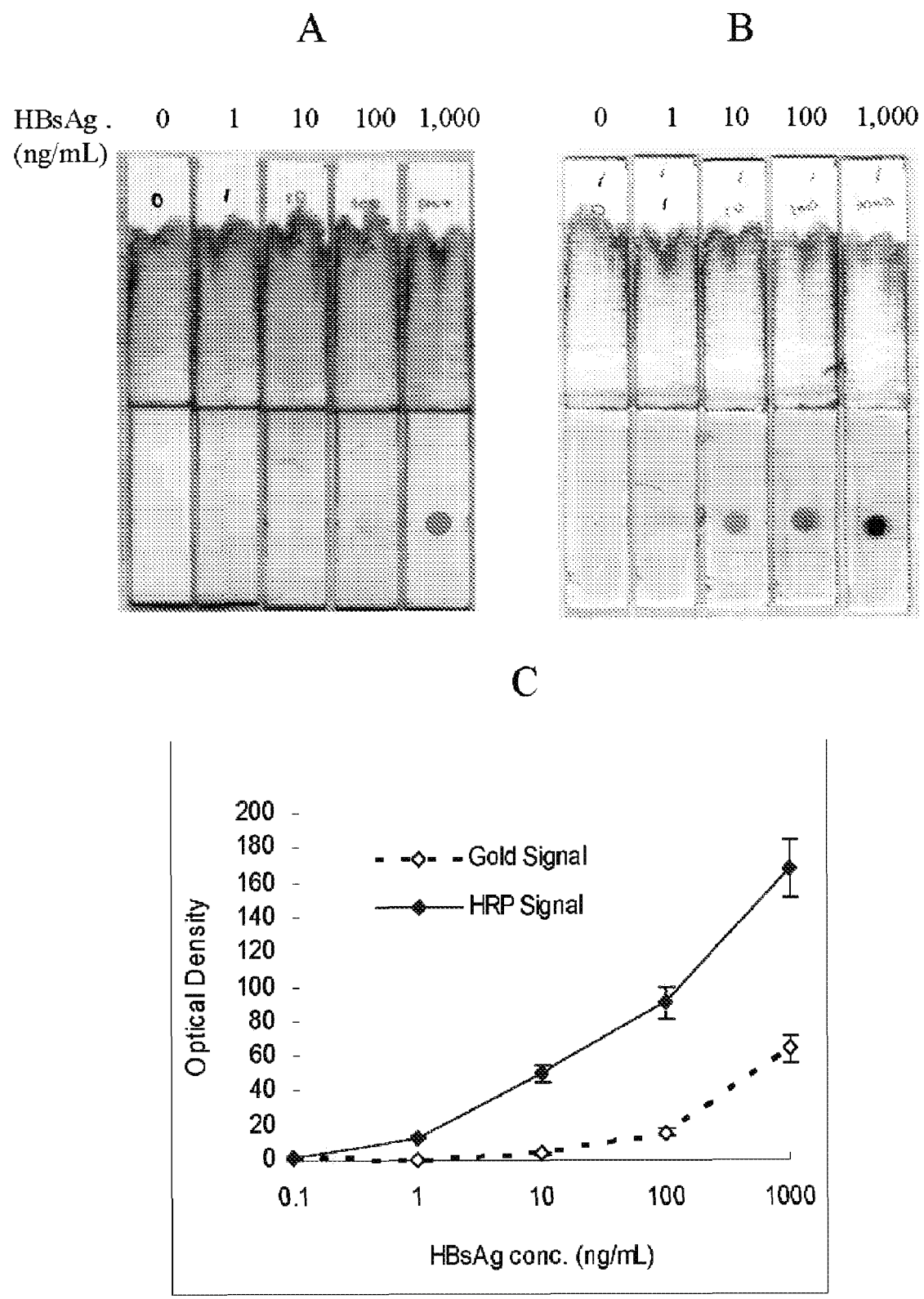
FIG. 8 shows responses of the color detection-type photometric biosensor (Example 6) according to the present invention against the concentration of analyte (Hepatitis B virus surface antigen, HBsAg). A reveals the experimental results using gold colloids as label, B those using an enzyme, HRP, as label, and C the dose-response curves expressed the color signals in optical density.

Dose Responses of Color Detection-type Photometric Biosensor 6-1. Use of Gold Colloids as Tracer Gold color signal as dose response of the analytical system prepared in Example 5 to HBsAg standard was determined by scanning reflectance photometry. Each standard solution of HBsAg (150 µl) was placed into different microwells, the immuno-strips were placed into each microwell in an erect position to adsorb the aqueous solutions into the strips for 15 min. The signal appeared at the area of the immobilized antibody was scanned by a scanner (HP ScanJet 6100C, Hewlett-Packard, Palo Alto, Calif., USA). The colored area on the captured image (FIG. 8, A) was selected by using image analysis program (Multianalyst version 1.1, Bio-Rad Laboratories, Hercules, Calif., USA) such that all of the colored area can be covered, and then converted to optical density that was in proportion to color intensity (FIG. 8, C Gold signal).

Based on the results, the optical density measured as well as the color intensity recognized by naked eyes were proportional to the analyte concentration. In case of the gold color signal, detection sensitivity was about 100 ng/ml.

6-2. Use of HRP as Tracer

HRP signal as dose response to HBsAg from an assay system constructed as described in Example 5-1 was determined using the same method as for gold color signal measurement. The analytical procedure was basically identical to those for producing gold signal except the additional use of secondary antibody-HRP conjugate as mentioned. For HRP signal generation, the substrate supplying pad and absorbent pad in the horizontal arrangement were positioned to the right and left side of the signal pad, respectively, and the substrate solution for HRP was supplied to allow the progress of horizontal flow for 3 min. Remaining components except the immune complexes captured by the capture antibody on the NC membrane were removed and at the same time a blue color signal was generated from HRP included in the captured immune complexes (FIG. 8, B).

The color signal was quantified to optical density using the same procedure as for the gold signal (FIG. 8, C HRP signal).

From the results obtained, the optical density as signal was in proportion to the color intensity recognized by naked eyes and also proportional to the analyte concentration. In case of use of the enzyme as tracer, the detection sensitivity was about 1 ng/ml and this was about 100-fold superior over that of the gold color signal (FIG. 8, C).

Example 7

Construction of Light Detection-type Analytical System 7-1. Construction of Immuno-strip As a model analyte, a specific marker for acute myocardial infarction cardiac troponin I, was used. An immuno-chromatographic assay system was constructed using capture antibody-biotin conjugate, detection antibody-gold colloid conjugate or detection antibody-ARP conjugate and membrane strip with immobilized SA prepared in Example 4. The immuno-strip (FIG. 1) includes, from the bottom end, a glass fiber membrane (7×20 mm) treated with 0.1% (v/v)

Triton X-100, a glass fiber membrane (7×5 mm) with the conjugates, a NC membrane (7×25 mm) with immobilized SA, and a cellulose membrane (7×15 mm) as absorbent pad. Each contiguous membrane strip were partially superimposed and fixed on a plastic film by a double-sided tape.

7-2. Construction of Horizontal Arrangement Pads

For the generation of a light signal from ARP present on the strip, the horizontal arrangement pads were constructed using a glass fiber membrane (10×20 mm) for supplying the enzyme substrate solution containing luminol and hydrogen peroxide, and a cellulose membrane (15×20 mm) as absorption pad. The role of the horizontal arrangement pads is already mentioned in Example 5-2 and also shown in FIG. 2.

Example 8

Figure 9:
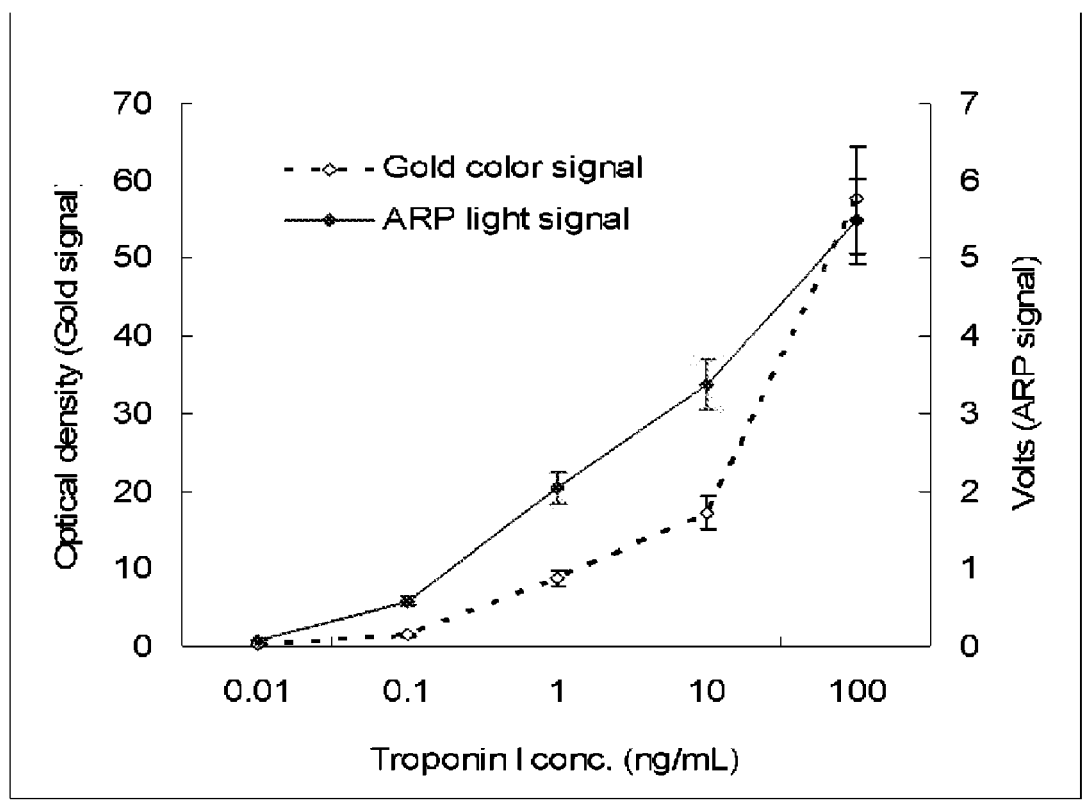
FIG. 9 shows a comparison of gold color signal and ARP light signal against the standard concentrations of analyte, cardiac Troponin I. The light signals were determined using a light detection-type membrane strip biosensor prepared in Example 7.

Dose Response of Light Detection-type Biosensor 8-1. Use of Gold Colloids as Tracer Gold color signal as dose response of the analytical system prepared in Example 7-1 to cTn I standard was determined by scanning reflectance photometry. Each standard solution of cTn I (150 μl) was placed into different microwells, the immuno-strips were placed into each microwell in an erect position. The next analytical procedure was the same as that for HBsAg in Example 6-1, and the color signal produced was converted to optical density as also demonstrated (FIG. 9, Gold color signal).

It was observed based on the results that the optical density was in proportion to the color intensity recognized by naked eyes and also proportional to the analyte concentration. In case of the gold color signal, the detection sensitivity was about 1 ng/ml.

8-2. Use of ARP as Tracer

ARP light signal as dose response to cTn I was measured from an assay system constructed identically with the gold color detection-type immuno-strip as described in Example 8-1 except the use of detection antibody-ARP instead of detection antibody-gold colloid conjugate and also the use of cross-flow as the key idea for the generation of signal from enzyme in the present invention. The procedure for immune reactions in the vertical flow mode was identical with that of Example 8-1 using gold colloids as tracer. After the completion of the vertical flow, the substrate supply pad and absorbent pad in the horizontal arrangement were positioned to the right and left side of the signal pad, respectively, an the substrate solution for ARP, 0.2 M carbonate buffer, pH 9.0, containing hydrogen peroxide and luminol was supplied to allow the progress of the horizontal flow for 3 min. The remaining components except the immune complexes captured on the membrane was removed and at the same time a blue light signal was generated from ARP included in the captured immune complexes. The light signal was quantified using photodiode (Hamamatsu, Japan) and analog-digital conversion device (ADCM board, manufactured in Korea) installed within a personal computer.

It was observed based on the results that an electric signal (voltage) converted from the light signal was in proportion to the analyte concentration (FIG. 9, ARP light signal). The detection sensitivity was about 0.1 ng/ml and this was about 10-fold superior over that of using gold colloids as tracer.

Example 9

Construction of Electrochemical Detection-type Analytical System

Figure 6:
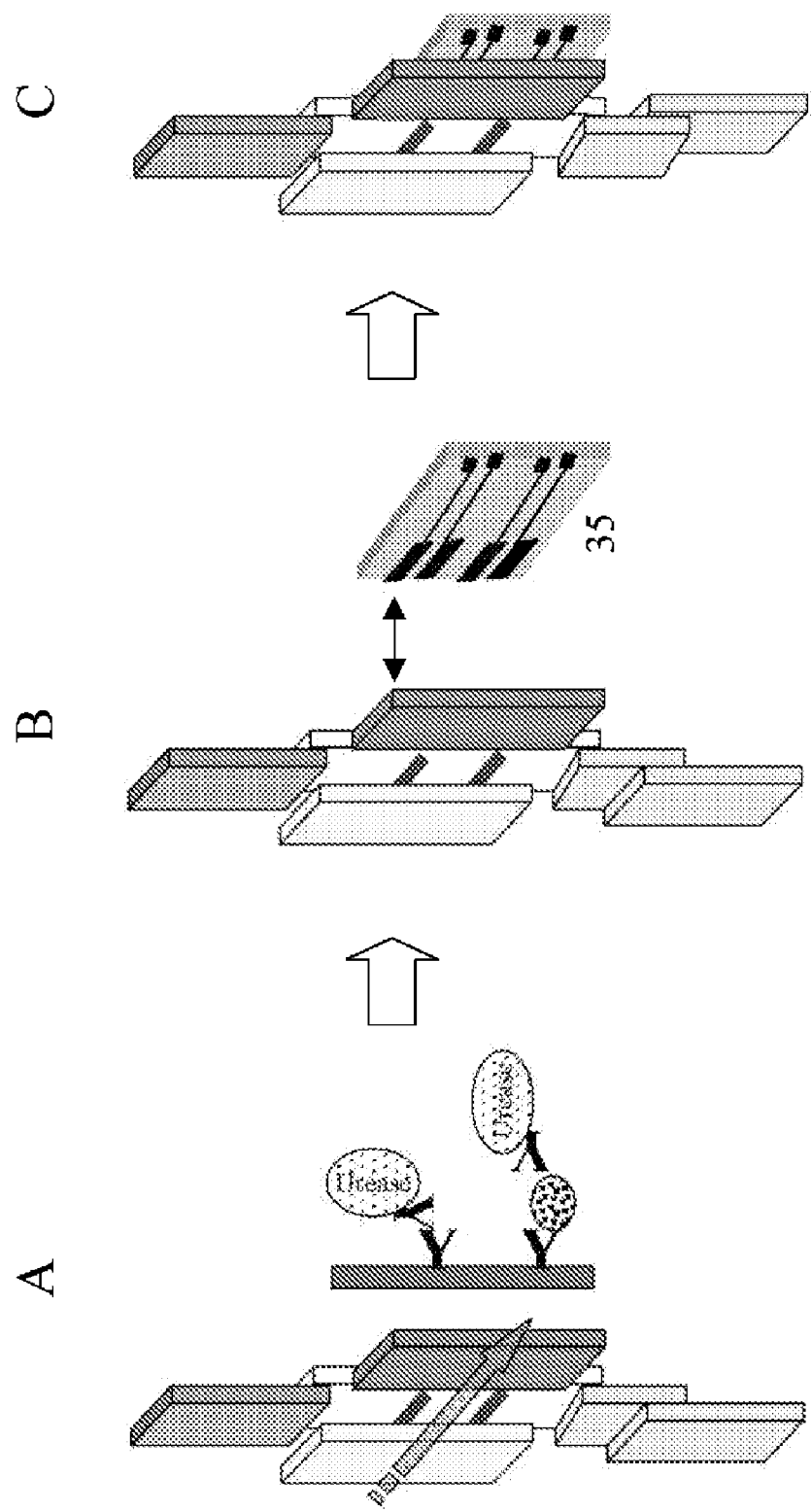
FIG. 6 shows the analytical principle of an electrochemical biosensor in the present invention, which utilizes the same principle as described in FIG. 4 except signal generation. Herein, A describes enzymatic reaction for signal generation, B electrode attachment procedure, C a electrochemical signal (e.g., conductivity change) detection.
Figure 7:
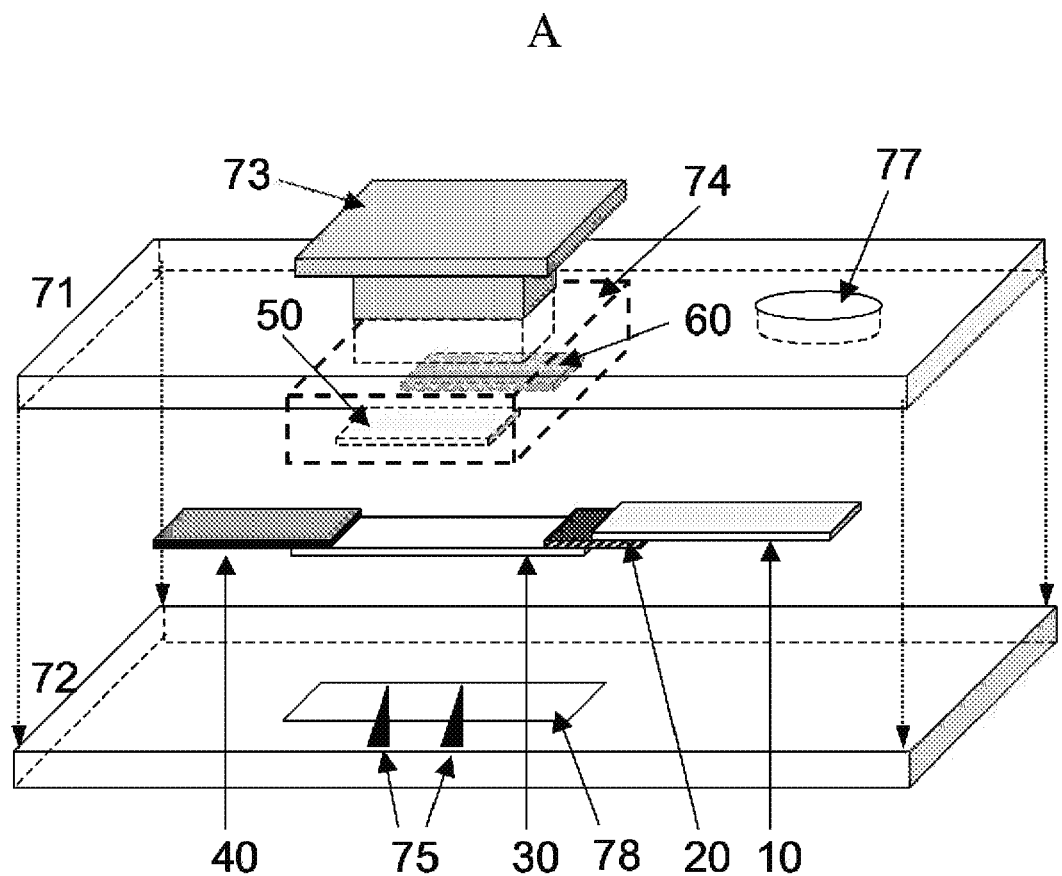
FIG. 7 shows a holder of the analytical components for the cross-flow membrane strip chromatographic assay, which is designed to perform the sequential processes, i.e., the immune reaction and enzymatic reaction, in an automatic or manual mode. Herein, A and B depict the overall constitution of the holder, C and D depict cross-section of the holder with the top and bottom plates of the holder being combined. Partially, C depicts the relative position of the horizontal and vertical arrangement pads during the progress of vertical flow for immune reactions, and D depicts the relative position of the two arrangement pads during the progress of horizontal flow for enzymatic reaction.
Figure 7:
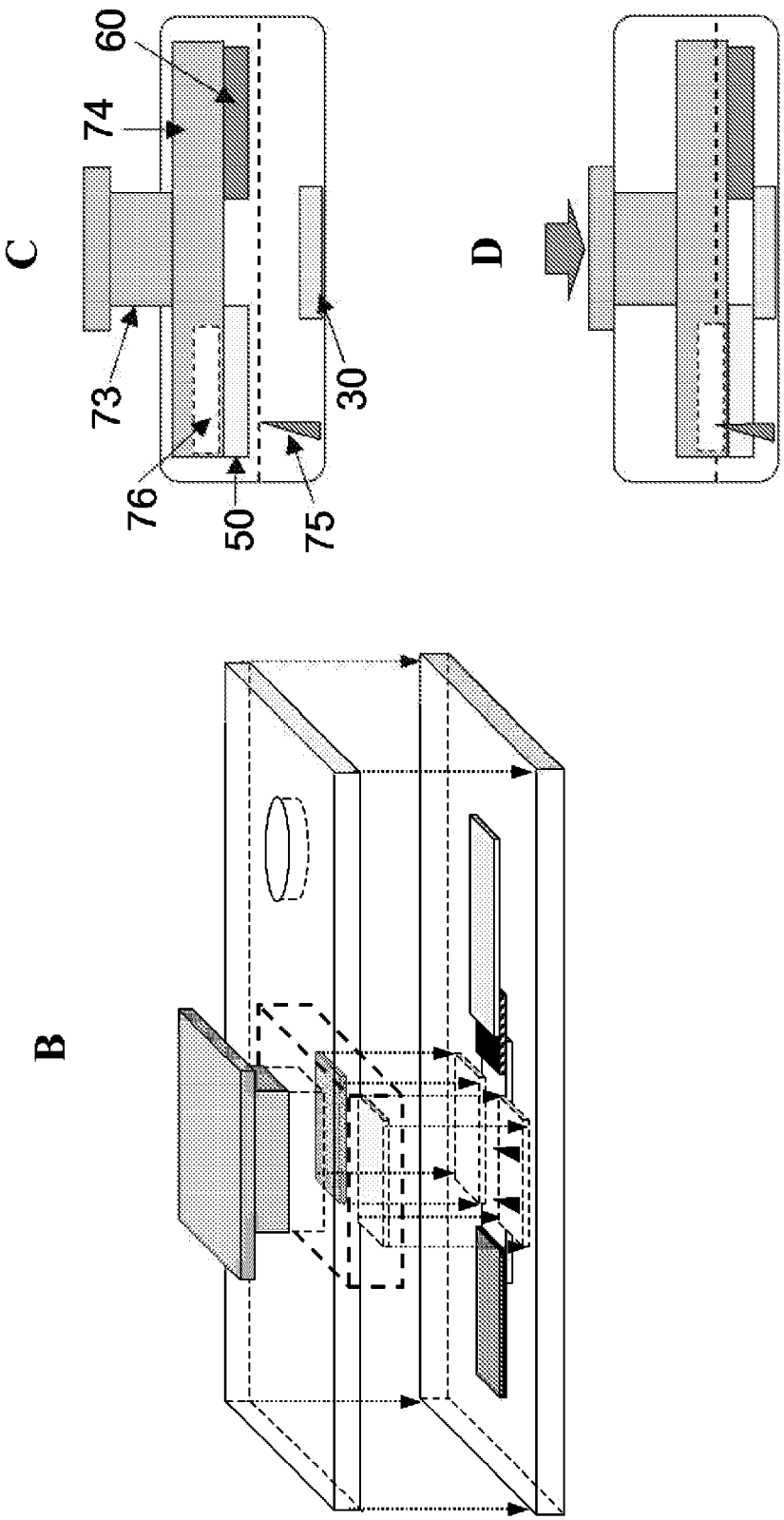

An immuno-chromatographic assay system producing electrochemical signal against the analyte concentration, was constructed according to basically identical procedure to those shown in Examples 5 and 7. The electrochemical detection system however, additionally required electrode as shown in FIG. 6 and, to demonstrate on an electrochemical measurement, a conductivity detection system is explained below.

9-1. Construction of Immuno-strip

As a model analyte, human serum albumin (HAS) which is used as a marker for early diagnosis of renal disease resulting from complication of diabetes mellitus, was employed. An immuno-chromatographic assay system was constructed using detection antibody-urease conjugates and a NC membrane strip with the immobilized capture antibody. The immuno-strip system (FIG. 1) was constructed in the same manner as that descried in Example 5-1.

9-2. Construction of horizontal Arrangement Pads

For the generation of a conductivity signal from urease present on the strip, the horizontal arrangement pads were constructed using a glass fiber membrane (10×20 mm) for supplying the enzyme substrate solution containing urea and a cellulose membrane (15×20 mm) as absorption pad.

Example 10

Dose Response of Electrochemical Detection-type Biosensor

Figure 10:
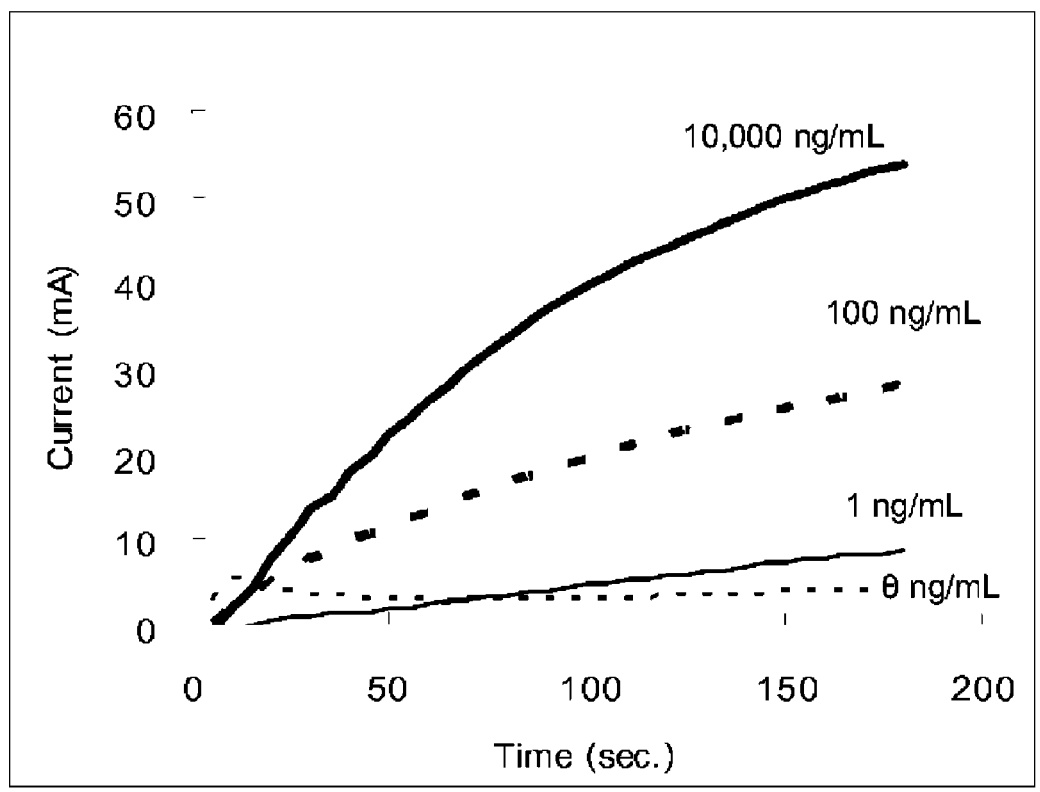
FIG. 10 shows conductivity signal change against the standard concentration of human serum albumin, which was determined using a conductimetric membrane strip biosensor prepared in Example 9 to demonstrate an application of the concept into an electrochemical biosensor.

Dose response to HSA from the assay system prepared in Example 9 was obtained using an electrochemical detection device (e.g., conductivity meter). The same analytical procedure was employed as described in Example 6-2. After applying the horizontal flow for 3 min, the remaining components except the immuno-complexes captured on the membrane were removed, and, at the same time, urease included in the immune complexes decomposed urea to produce ammonium ion and carbonium ion. Thus, a conductivity change in proportion to the analyte concentration appeared as signal (FIG. 10). The conductivity signal expressed in current generated at the area with the immobilized capture antibody was then measured by a digital multimeter (HITASI, Japan).

It was demonstrated based on the results that the conductivity dependent current was proportional to the analyte concentration and the detection sensitivity was conformed to be about 1 ng/ml.

Example 11

Enzyme Labeling Method

There are two labeling methods in enzyme-linked immunosorbent assay (ELISA), that is, direct method where signal is generated by directly attaching an enzyme to the detection antibody reacting specifically to analyte and indirect method where the detection antibody is used intactly for binding to analyte and an enzyme is attached to a secondary antibody that specifically recognizes the detection antibody for signal generation.

By using the cross-flow system that was employed to introduce enzyme-based signal amplification technique to membrane strip analytical system, as in ELISA, the two labeling methods were compared. The direct labeling method was applied by directly attaching HRP to the detection antibody, monoclonal antibody produced from mouse specific to HBsAg (analyte), and the indirect labeling method was tested by attaching HRP to a secondary antibody, a polyclonal antibody produced from goat which recognized the detection antibody specific to analyte. Basically, the direct method may require that the enzyme label should be attached to each detection antibody for different analytes. On the other hand, the indirect method is advantageous for convenience and signal amplification, that is, the enzyme conjugate can be used even for different analytes, and signal amplification can be achieved owing to the use of the additional antibody. In this example, the two methods were used to compare their analytical performances.

Figure 11:
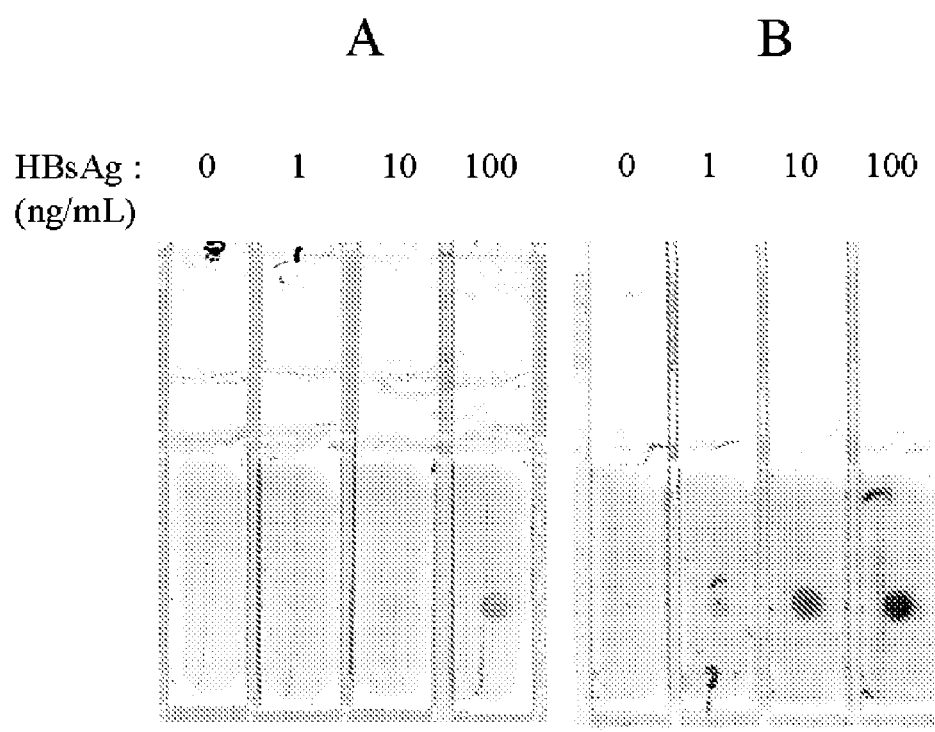
FIG. 11 shows a comparison of dose responses to HbsAg measured by a direct enzyme-labeling method and indirect method. A and B are the results of color signal produced from the membrane strip biosensor system based on the cross-flow concept according to the direct and indirect methods, respectively, and C shows the results of color signal produced from enzyme-linked immunosorbent assays (ELISA) and measured at the absorbance of 450 nm.
Figure 11:
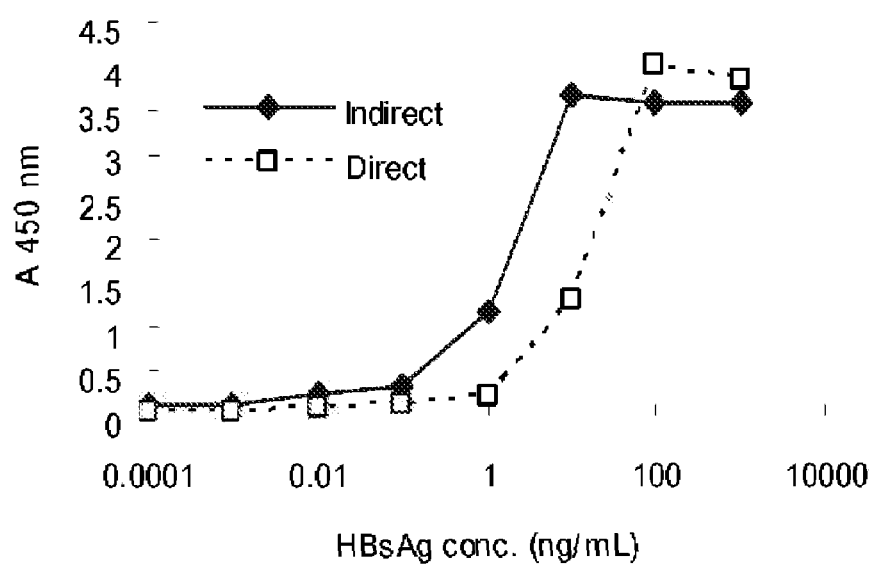

Analysis employing the indirect labeling method was conducted identically to that in Example 6-2, and assay using the direct method was carried out as described in Example 6-1 except the use of HRP, instead of gold, attached to the detection antibody specific to HBsAg. Dose responses of the membrane strip assay systems to HBsAg standard were determined as explained above by the scanning photometry for the color signals generated (FIGS. 11, A and B).

From the results, for the direct and indirect methods, respectively, it was demonstrated that the detection sensitivity of the indirect method was about 10-fold higher than that of the direct method. The same comparative results were also obtained from ELISA (FIG. 11, C). However, depending on the purpose of analyses and requirements, a preferential method can be varied.

INDUSTRIAL APPLICABILITY

The present invention provides a membrane strip biosensor technology that not only enables a quick and simple assay required for point-of-care testing but also satisfies a clinical need for highly sensitive detection of analyte within specimen. These were achieved by applying the principle of laboratory-version enzyme-linked immunosorbent assay to a device for point-of-case testing, providing advantages of cheap and sensitive quantitation of analyte.

The invention claimed is:

1. A membrane strip biosensor system comprising:
    (a) a first group of membrane pads comprising:
        (i) a first membrane pad for sample application,
        (ii) a second membrane pad for release of a detection binding component, said second membrane pad comprises a tracer-linked binding component specific for and able to bind to an analyte in said sample to form an analyte/binding component complex,
        (iii) a third membrane pad that is a signal generation membrane pad with an immobilized binding component specific for and able to capture said analyte/binding component complex,
        (iv) a fourth membrane pad for absorption of flow medium;
    (b) a second group of membrane pads comprising:
        (vi) a fifth membrane pad for the supply of a substrate solution,
        (vii) a sixth membrane pad for absorption of excess substrate solution, and
    (c) substrate solution;
        wherein the system has a cross-arrangement of the two groups of membrane pads:
        said first group of membrane pads is arranged in a first flow direction wherein said first membrane pad is partially superimposed and fixed at an end of said second membrane pad, and said second membrane pad and said fourth membrane pad are partially superimposed and fixed one at each end of the third membrane pad, and wherein said sample is applied to said first membrane pad and flows laterally along said second and third membrane pads to said fourth membrane pad to comprise a first flow reaction; and
        said second group of membrane pads is arranged in a second flow direction perpendicular to the first flow direction, wherein said fifth and sixth membrane pads are partially superimposed and fixed at both lateral sides of the third membrane pad to form a pathway for a second flow reaction.

2. The membrane strip biosensor system in claim 1, wherein for an electrochemical determination, said signal generation membrane pad further comprises an electrode.

3. The membrane strip biosensor system of claim 1, wherein the system further comprises a container for holding said substrate solution.

4. The membrane strip biosensor system in claim 1, wherein the said first membrane pad for sample application, said second membrane pad for release of detection binding component, and said fifth membrane pad for the supply of substrate solution are glass fiber membranes, the signal generation membrane pad is a nitrocellulose membrane, and said fourth and sixth membrane pads for absorption are a cellulose membranes.

5. The membrane strip biosensor system in claim 1, wherein the tracer-linked binding component for detection comprises either
    i) a conjugate of a tracer with a first binding component, or
    ii) a first binding component and a conjugate of a tracer with a second binding component specific to the first binding component.

6. The membrane strip biosensor system in claim 5, wherein the binding component for detection is selected from the group consisting of an antibody, an enzyme, a receptor, and DNA that reacts specifically with an analyte in said sample.

7. The membrane strip biosensor system in claim 5, wherein the tracer is an enzyme selected from the group consisting of horseradish peroxidase, alkaline phosphatase, β-galactosidase, and arthromyces ramosus peroxidase and the substrate solution comprises a chromogenic substrate component specific to said enzyme, and, at the time of signal generation, color change detectable with naked eyes is shown as signal as the result of an enzyme-substrate reaction.

8. The membrane strip biosensor system in claim 5, wherein the tracer is gold colloids and the substrate solution comprises a silver compound, and, at the time of signal generation, color change detectable with naked eyes is shown as signal by chemical catalytic reaction.

9. The membrane strip biosensor system in claim 5, wherein the tracer is horseradish peroxidase or arthromyces ramosus peroxidase and the substrate solution comprises luminol or other luminescent substrate components specific to an enzyme, and at the time of signal generation, a light signal is measured as signal generated by enzyme-substrate reaction.

10. The membrane strip biosensor system in claim 5, wherein the tracer is $Co^{2+}$, $Cu^{2+}$, $Mg^{2+}$, $Fe^{2+}$ or their compounds and the substrate solution comprises luminol or other luminescent substrate component, and at the time of signal generation, a light signal is measured as signal generated by chemical catalytic reaction.

11. The membrane strip biosensor system in claim 5, wherein the tracer is glucose oxidase, urease, penicillin oxidase, or cholesterol oxidase and the substrate solution comprises an electrochemical signal-generating component specific to an enzyme, and, at the time of signal generation, conductivity change, current change, or voltage change is measured as signal generated by enzyme-substrate reaction.

12. The membrane strip biosensor system in claim 1, wherein the binding component for capture is selected from the group consisting of an antibody, an enzyme, a receptor, or a DNA which reacts specifically with said analyte or with said analyte/binding component complex.

13. A biosensor membrane strip system having a plurality of membrane pads in fluid communication, said system comprising:
  (a) an immuno-strip comprising
    (1) a sample application membrane pad;
    (2) a detection reagent-releasing membrane pad positioned to receive sample from said sample application membrane pad, said detection reagent-releasing membrane pad comprising a mobilizable labeled specific binding reagent for binding to an analyte in said sample to form an analyte/detection reagent complex, wherein said mobilizable labeled detection reagent is freely soluble or dispersible in said sample and is free to move with said sample along said detection reagent-releasing membrane pad, whereby it is transported by said sample from said detection reagent-releasing membrane pad to a signal generation membrane pad;
    (3) a signal generation membrane pad downstream of said detection reagent-releasing membrane pad, said signal generation membrane pad comprising an immobilized capture reagent for binding to said analyte/detection reagent complex; and
    (4) a first absorbent membrane pad downstream of said signal generation membrane pad;
  wherein said sample application membrane pad, detection reagent-releasing membrane pad and signal generation membrane pad overlap at their adjacent ends to provide effective contact between the pads thereby forming a first flow path; and
  (b) an enzyme substrate solution flow strip comprising:
    (5) a substrate solution membrane pad; and
    (6) a second absorbent membrane pad,
  wherein said substrate solution membrane pad and said second absorbent membrane pads, when brought into fluid communication with said signal generation membrane pad of said immunostrip, form a second flow path that is different from the first flow path.

14. The biosensor membrane strip system of claim 13, wherein said first flow path along said immuno-strip is perpendicular to said second flow path.

15. The biosensor membrane strip system of claim 13, wherein said first fluid flow path is in the same direction as said second fluid flow path.

* * * * *

UNITED STATES PATENT AND TRADEMARK OFFICE
CERTIFICATE OF CORRECTION

PATENT NO. : 7,300,802 B2  Page 1 of 1
APPLICATION NO. : 10/827884
DATED : November 27, 2007
INVENTOR(S) : Paek et al.

It is certified that error appears in the above-identified patent and that said Letters Patent is hereby corrected as shown below:

In The Claims:

Claim 1, Col. 19, line 62: insert --a-- before "substrate solution".

Claim 4, Col. 20, line 26: delete "absorption are a" and insert --absorption are--.

Claim 13, Col. 22, line 18: delete "membrane pads" and insert --membrane pad--.

Signed and Sealed this

Twenty-ninth Day of April, 2008

JON W. DUDAS
*Director of the United States Patent and Trademark Office*